United States Patent
Sumitomo et al.

(10) Patent No.: US 8,540,757 B2
(45) Date of Patent: Sep. 24, 2013

(54) PHOTOTHERAPY APPARATUS USING EXCIMER RADIATION

(75) Inventors: Taku Sumitomo, Himeji (JP); Tatumi Hiramoto, Tokyo-to (JP); Akimichi Morita, Nagoya (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 912 days.

(21) Appl. No.: 11/610,130

(22) Filed: Dec. 13, 2006

(65) Prior Publication Data

US 2007/0135872 A1 Jun. 14, 2007

(30) Foreign Application Priority Data

Dec. 13, 2005 (JP) .................... 2005-359327

(51) Int. Cl.
*A61N 5/06* (2006.01)
(52) U.S. Cl.
USPC ............. 607/88; 607/90; 607/94; 606/3
(58) Field of Classification Search
USPC ............. 607/88–94, 96; 606/3–13; 128/898
See application file for complete search history.

(56) References Cited

U.S. PATENT DOCUMENTS

| | | | |
|---|---|---|---|
| 5,165,773 A * | 11/1992 | Nath | 362/574 |
| 5,433,942 A * | 7/1995 | Wood et al. | 424/59 |
| 5,955,840 A | 9/1999 | Arnold et al. | |
| 6,413,268 B1 | 7/2002 | Hartman | |
| 6,436,127 B1 * | 8/2002 | Anderson et al. | 607/89 |
| 6,514,243 B1 * | 2/2003 | Eckhouse et al. | 606/9 |
| 6,979,327 B2 | 12/2005 | Spencer | |
| 7,144,248 B2 | 12/2006 | Irwin | |
| 2003/0216795 A1 * | 11/2003 | Harth et al. | 607/88 |
| 2004/0249369 A1 * | 12/2004 | Muzzi et al. | 606/9 |
| 2005/0143793 A1 * | 6/2005 | Korman et al. | 607/94 |
| 2010/0234926 A1 * | 9/2010 | Spencer | 607/89 |

FOREIGN PATENT DOCUMENTS

| | | |
|---|---|---|
| DE | 101 62 147 A1 | 7/2003 |
| JP | 63-119780 A | 5/1988 |
| JP | 2004-242790 A | 9/2004 |
| JP | 2005-312768 A | 11/2005 |
| WO | 03 024526 A1 | 3/2003 |
| WO | 03/047682 A2 | 6/2003 |
| WO | 2004/062728 A1 | 7/2004 |
| WO | 2005/015291 A2 | 2/2005 |
| WO | 2005/104162 A2 | 11/2005 |

* cited by examiner

*Primary Examiner* — Ahmed Farah
(74) *Attorney, Agent, or Firm* — Roberts Mlotkowski Safran & Cole, P.C.; David S. Safran

(57) ABSTRACT

A phototherapy device using excimer radiation in which, by skillful use of the individual peak wavelength of 308 nm and of the emission range of shorter wavelengths than 308 nm, the therapy effect is enhanced, and in which, at the same time, harm can be reduced is achieved using a XeCl excimer lamp and in which diseased sites of skin disorders are irradiated with UV-B radiation with an optical filter being used for changing the spectral shape of the UV-B radiation with which the diseased sites are irradiated.

10 Claims, 8 Drawing Sheets

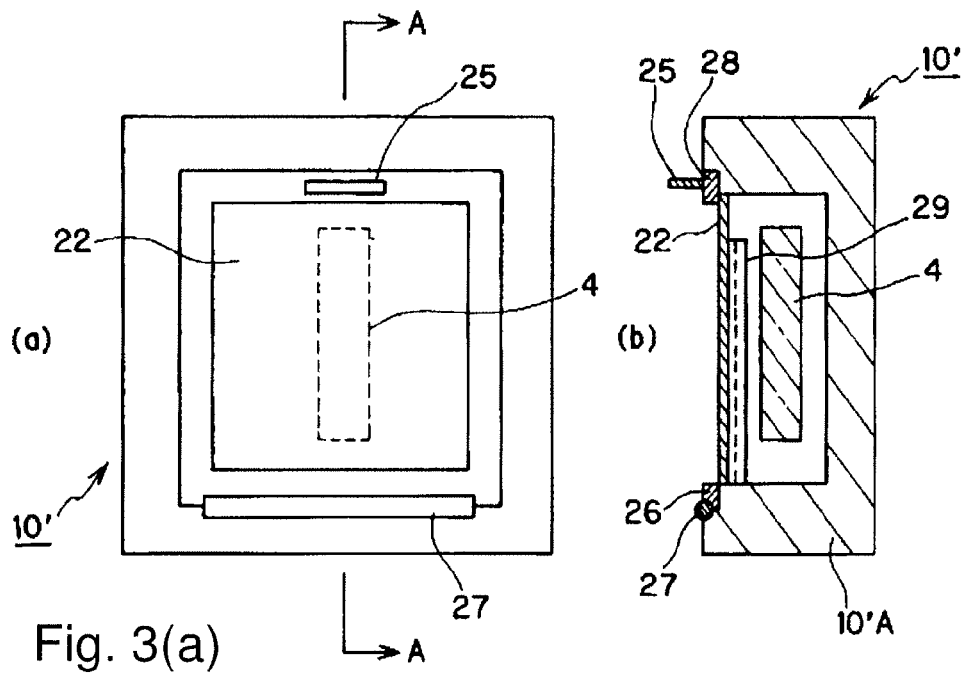
Fig. 3(a)
Fig. 3(b)
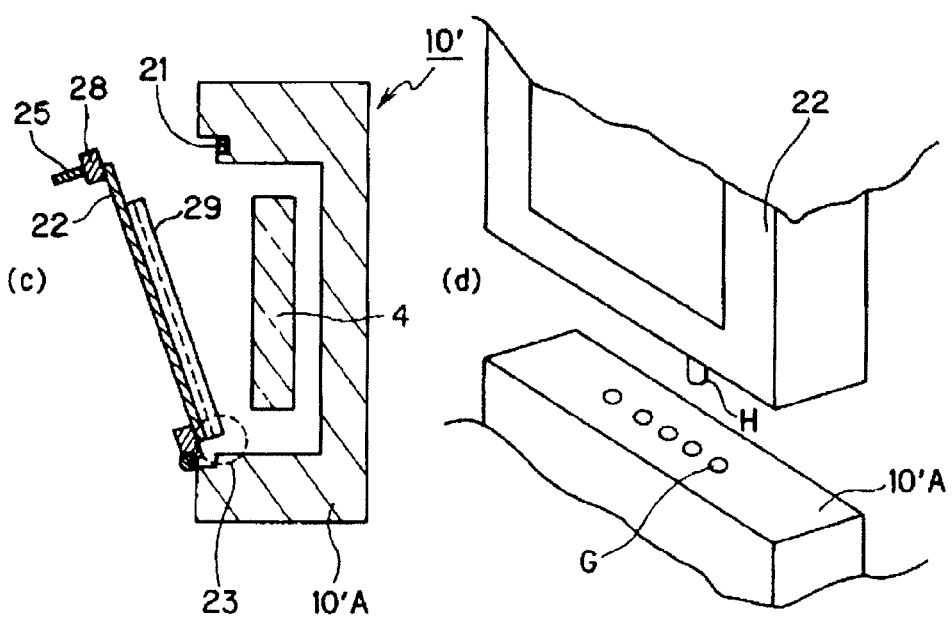
Fig. 3(c)
Fig. 3(d)

PHOTOTHERAPY APPARATUS USING EXCIMER RADIATION

BACKGROUND OF THE INVENTION

1. Field of the Invention

The invention relates to a phototherapy device for treatment of skin disorders by irradiation with UV radiation in the UV-B range (280 nm to 320 nm).

2. Description of Related Art

Among skin disorders there are various conditions, such as psoriasis, atopic dermatitis, vitiligo and the like. In this section, psoriasis is described as a typical example. The mechanism of psoriasis is still not clarified. Some treatment methods have been proposed for it, and they are applied. However, no therapy has been found for complete healing of diseased sites of all patients. The aforementioned treatment methods are used only to suppress the outbreak of the disorder. These therapy methods are largely classified in three methods, specifically topical remedies, phototherapy and oral remedies.

In topical remedies, generally steroid medicine for topical application, vitamin $D_3$ pharmaceuticals and the like are used. Steroid medicines for topical use lead to dermal atrophies and the like when used over a long time. Vitamin $D_3$ pharmaceuticals for topical application must be used with consideration of daily application frequencies and the like.

As oral remedies, retinoid, cyclosporin, and the like are used. These pharmaceuticals for oral application suppress anomalous proliferation of the skin and weaken immune reactions. Therefore, they have the disadvantage that they act not only on diseased sites, but also outside of diseased sites. As a result, it is difficult to use them for treatment of patients with especially severely diseased sites.

In phototherapy, there is a process using UV-A (320 nm to 400 nm) and a process using UV-B. The therapy process using UV radiation in the UV-A range is generally called PUVA therapy, it being used together with a photosensitive pharmaceutical called psoralen. After oral or topical use of psoralen, or after bathing in a psoralen-containing liquid, UV radiation in the UV-A range is applied, with the consequence of difficulties in daily life, such as sun after therapy and the like must be avoided. The therapy process using UV-B range is conversely a simple process in which treatment can be performed without using psoralen. Recently, a narrow-band UV-B method therapy has been noted in which diseased sites are irradiated only with an especially effective UV-B wavelength range.

The UV light source in narrow-band UV-B therapy is a fluorescent lamp with spectral lines at 311 nm to 313 nm. The appearance and basic arrangement of the fluorescent lamp are identical to those of fluorescent lamps for general illumination purposes. Only the types of phosphors for converting UV radiation from mercury vapor which is contained in the fluorescent lamp into other wavelengths differ from one another. Phosphor-containing gadolinium as the activating agent is used as this phosphor. Expressed conversely, sharp emission spectra of 311 nm to 313 nm are radiated because phosphor-containing gadolinium as the activating agent is used. There is also, to some extent, an indication of the possibility of increasing the therapy effect at a somewhat shorter wavelength, for example, at an emission wavelength of about 305 nm. However, since essentially there is no phosphors in this range which emits intensively, in practice, narrowband UV-B therapy using a fluorescent lamp with spectral lines at 311 nm to 313 nm is performed.

In view of this situation, a new light source for narrow-band UV-B therapy has been suggested. There is a XeCl excimer lamp using XeCl excimer radiation in which the individual peak wavelength is 308 nm. FIGS. 5(a) & 5(b), each show an emission spectrum example of this light source. The characterizing feature thereof is that the wavelength peak is at 308 nm, and that short wavelengths of less than 300 nm are also emitted, as is radiation with short wavelengths which are not emitted in a fluorescent lamp for narrow-band UV-B therapy. Whether this radiation with short wavelengths acts effectively is not completely clear. To some extent, however, it has already been reported that, at diseased sites at which no therapy effect was confirmed with a conventional fluorescent lamp, therapy effects were confirmed by the XeCl excimer lamp. Phototherapy with a XeCl excimer lamp is disclosed in International Patent Application Publication WO 03/024526 A and U.S. Pat. No. 5,955,840.

In addition to the above described therapy effect, the XeCl excimer lamp also has the following advantages. Within the fluorescent lamp the UV radiation from the mercury which has been heated and vaporized during operation by the discharge is converted by the phosphors into emissions from 311 nm to 313 nm so that the intensity changes depending on the degree of vaporization of the mercury which is liquid prior to operation. In narrow-band UV-B therapy, the duration of irradiation is at most a few minutes each time. The intensity within a few minutes after the start of lamp operation changes by some 10%, by which control of the duration of irradiation of the diseased site is difficult. On the other hand, the XeCl excimer lamp, due to the gaseous state of lamp contents before operation, has a slight change of intensity after the start of lamp operation so that control of the duration of the irradiation of diseased sites is simple.

Compared to a fluorescent lamp, the XeCl excimer lamp can be operated with a higher power density so that diseased sites can be irradiated with a high illuminance. This means that, in this connection, a shortening of the duration of therapy can be expected. Since diseased sites are irradiated with a constant amount of irradiation in a well controlled manner, the patient is prohibited from moving the diseased sites during the therapy duration. Shortening of the length of therapy is therefore an important improvement for reducing the burden on the patient.

As was described above, in the phototherapy device (hereinafter phototherapy device using excimer radiation) in the UV-B range with a light source which is a XeCl excimer lamp, the radiant light from the lamp has an individual peak wavelength of 308 nm because excimer emission is used for this purpose. The potential of this device as a phototherapy device which is effective for treatment is being considered.

It is mentioned that light in the UV-B range which is effective for treatment of skin disorders has two aspects, specifically the therapy effect and side effects (harm). One side effect relates to formation of erythemas on the skin. The above described phototherapy device using excimer radiation carries out radiation with two aspects: specifically, the therapy effects and side effect (harm) since the spectrum with an individual peak wavelength has a wide emission range with FWHM (full width at half maximum) of at least 20 nm. On the other hand, since the emission in the vicinity of 310 nm has a negligibly small side effect, while the therapy effect is also weak, therapy was performed by irradiation over a long time interval. Recently, it has become increasingly clear that UV radiation with shorter wavelengths has a greater therapeutic effect. Furthermore, it has been found that there are cases in which, depending on individually differences of symptoms of skin disorders, UV radiation in the UV-B range in the vicinity of 310 nm has hardly any therapeutic effect.

SUMMARY OF THE INVENTION

A primary object of this invention is to devise a phototherapy device using excimer radiation in which by skillful use of the individual peak wavelength of 308 nm and of the emission range on the side of shorter wavelengths than this, the therapy effect is enhanced and in which, at the same time, harm can be reduced.

The above described object is achieved in accordance with a first aspect of the invention in a phototherapy device using excimer radiation which has a XeCl excimer lamp and in which diseased sites of skin disorders are irradiated with UV-B radiation in that there is an optical filter unit for changing the shape of the spectrum of the UV-B radiation with which the diseased sites are irradiated.

The above described object is achieved in accordance with a further development in a phototherapy device using excimer radiation according to the first aspect of the invention in that the above described optical filter region has several optical filters, and by selection of at least one optical filter from these several optical filters and arranging it in the beam path, the shape of the spectrum of the UV-B radiation is changed.

The above described object is achieved in accordance with another development of the invention in a phototherapy device using excimer radiation according to the first aspect of the invention in that, in the above described optical filter region, at least one optical filter is selected from several optical filters which have been provided independently of the phototherapy device, and thus, the spectral shape of the UV-B radiation is changed, and this filter is placed.

The above described object is furthermore achieved in a phototherapy device using excimer radiation according to one of the above developments in that the above described several optical filters are made of the same material and that their thicknesses are varied.

The above described object is achieved in a development of the aforementioned aspect in that the above described optical filters are made of borosilicate glass.

The above described object is, moreover, achieved in that there is a device for controlling the amount of irradiation and the irradiation time according to the type of optical filter used.

The duration of irradiation for narrow-band UV-B therapy using a conventional fluorescent lamp is determined as follows, limited by the occurrence of erythema. The amount of UV-B irradiation at which erythema occurs differs depending on the skin type, the amount irradiated so far, and the like. Therefore, for each patient, before therapy, a patch test is performed, a patch test sheet with roughly five to ten square openings with a side length of roughly 2 cm being placed on the skin in the vicinity of the diseased site. This skin is irradiated with the narrow-band UV-B radiation, and for example, every five seconds after the start of irradiation, the square openings of the patch test sheet are closed one after the other. After 24 hours, the skin is observed. Based on the minimum irradiation duration at which erythema occurred, the minimum erythema dose (MED) can be determined. As was described above, for each patient, an optimum radiation amount is determined for which no erythema occurs as a side effect, and treatment starts.

Since the fluorescent lamp for narrow-band UV-B therapy has a sharp emission spectrum with a narrow FWHM, this has not been paid attention to date. The MED value, however, changes depending on the emission wavelength of the light source because the rate of occurrence of erythema changes according to wavelength. That is, the erythema characteristic which was determined in the fluorescent lamp differs from the erythema characteristic which is determined for the XeCl excimer lamp.

It is generally known that the MED value and the therapy effect characteristic with respect to wavelength appear as in FIG. 7. In this connection, the wavelength which can be used for therapy is a region in which the therapy effect predominates over the side effect (MED). A wavelength with a high value of the therapy effect is even more desirable since at a wavelength with a high therapy effect for a shorter irradiation duration a greater therapy effect is obtained, by which therapy can be finished in a shorter time and the burden on the patient can be reduced.

The characteristic of the therapy effect shown in FIG. 7 and the characteristic of the side effect differ like the MED value depending on the type of skin and the like, for each patient and each diseased site. When a diseased site is irradiated with uncontrolled radiant light from the XeCl excimer lamp, the diseased site is also irradiated with radiation with short wavelengths of roughly 280 nm. The characteristic shown in FIG. 7 is a general characteristic. Depending on the patient and the diseased site there are however cases in which the side effect exceeds the therapy effect.

In the actual treatment room, therefore, irradiation therapy in the following sequence is desired.

First, a filter or the like is placed between the lamp and the diseased site. The diseased site is irradiated with irradiation light for which the component of short wavelengths has been reduced as much as possible. Under these conditions, the MED value is determined and treatment is performed with a duration of irradiation for which no erythema occurs. If the irradiation duration determined in that way is too long, and the patient necessarily experiences pain, or if hardly any therapy effect is ascertained, the filter is replaced by a filter which transmits a component of shorter wavelengths. Then, in the same way, the MED value is determined, and treatment continues with a shorter interval of irradiation. By repeating the aforementioned process, the minimum wavelength with which the skin can be irradiated is determined. If the filter is selected in this way, effective therapy with a short duration is enabled. It does seem that it takes a very long time until the optimum filter is determined. However, since it is a therapy method in which psoriasis and the like are not completely cured, but their breakout is suppressed, therapy is needed over a longer time. The total duration of treatment is shortened as a result.

ACTION OF THE INVENTION

In accordance with the invention, a phototherapy device is devised which is suited for skin therapy with consideration of the different type of the patients and the skin disorders and enables optimum and moreover safe phototherapy.

The invention is further described below with reference to an embodiment shown in the accompanying drawings.

BRIEF DESCRIPTION OF THE DRAWINGS

FIGS. 3(*a*) to 3(*d*) each show a schematic of an irradiation unit of a phototherapy device using excimer radiation in which the operator replaces filters, FIG. 3(a) being a plan view, FIGS. 3(b) & 3(c) being sections taken along line A-A in FIG. 3(a) with the filter frame in closed and open positions, respectively, and FIG. 3(d) being a perspective view of the irradiation unit;

DETAILED DESCRIPTION OF THE INVENTION

Figure 1:
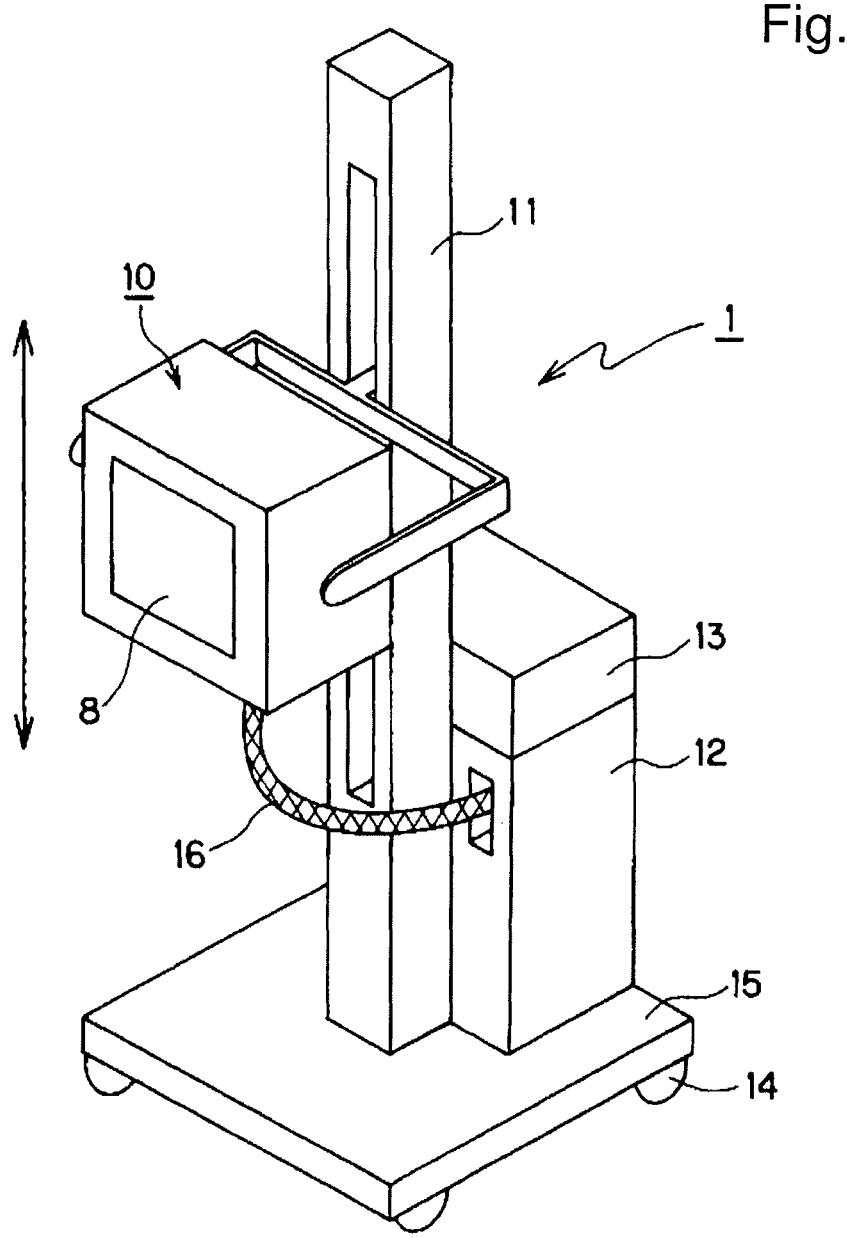
FIG. 1 is a schematic perspective view of the arrangement of one example of a phototherapy device in accordance with the invention using excimer radiation.

FIG. 1 is a schematic of the arrangement of one example of the phototherapy device 1 in accordance with the invention using excimer radiation, in which there is a XeCl excimer lamp and which has a light irradiation unit 10 which has an opening 8 through which UV-B radiation is emitted and for which, by moving the light irradiation unit 10 along a post 11 on a base frame 15 in the up and down arrow direction, excimer radiation can be emitted onto the desired region. The base frame 15 is provided with casters 14 and can move freely on the floor. On the base frame 15, there is a power source part 12 which supplies the irradiation unit 10 with power through a feed line 16 as controlled via a control panel 13.

Figure 4:
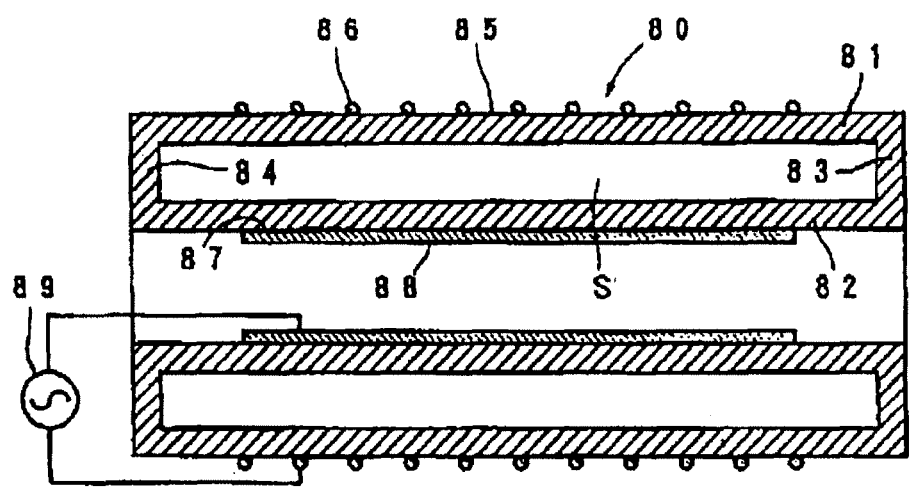
FIG. 4 is a schematic cross-sectional view of an excimer lamp which is used for the phototherapy device in accordance with the invention.

FIG. 4 is a schematic of an example of the arrangement of the excimer lamp which is located in the light irradiation unit 10 in a cross section. The excimer lamp shown is of the cylindrical tube type and radiation is emitted from its outer surface. The lamp has a discharge vessel 80 made of a dielectric of silica glass or the like which has a cylindrical outer wall 81 and a cylindrical inner wall 82 with a smaller outside diameter than inside diameter of the outer wall 81 and which is coaxially located inside of the wall 81. The two ends of the inner and outer walls 81, 82 are connected to one another by end walls 83, 84 so that a sealed cylindrical discharge space S is formed to which xenon chloride (XeCl) is added as a discharge gas.

A net-like electrode 86 of an electrically conductive material tightly adjoins the outer side 85 of the outer wall 81 of the discharge vessel 80. A film-like electrode 88 of aluminum is arranged to cover the outer side 87 of the inner wall 82. A high frequency power source 89 is connected to an electrode 86 and an electrode 88. In the above described discharge lamp, when a high frequency voltage is applied by a power source 89 between the electrodes 86, 88, in the discharge space S of the discharge vessel 80, a dielectric barrier discharge produces a host of microplasmas with a diameter of roughly 0.02 mm to 0.2 mm which yield excimers that are emitted from the discharge space S as excimer radiation that passes through the outer wall 81 and the net electrode 86 in the UV-B range with a peak of 308 nm.

Figures 2A, 2B:
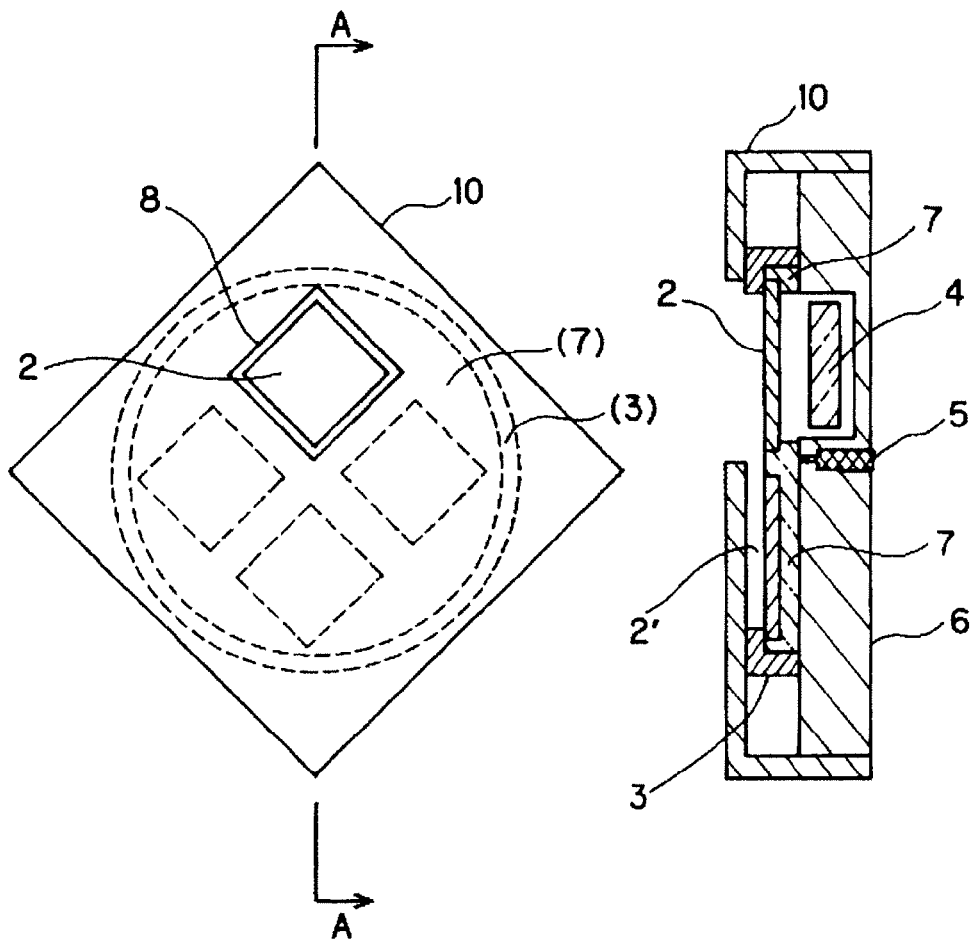
FIGS. 2(*a*) & 2(*b*) are schematic plan and sectional views, respectively, of an irradiation unit of a phototherapy device using excimer radiation which automatically replaces filters.

FIGS. 2(a) & 2(b) each schematically show the arrangement of the light irradiation unit 10. In the example shown, there are four types of filters that can be switched into position in front of the lamp 4. The holding device for the lamp is not shown in the drawings and can be of a conventional construction used for such lamps. The radiation emitted from the lamp 4 passes through the selected filter (filter 2 as shown) and is radiated to the outside from the light irradiation unit 10 through an opening 8. The four filters 2, 2' are mounted in grooves in a circular filter holding plate 7 which is rotated by a stepper motor 5 which is connected to the center axis thereof. From a control unit 13 of the phototherapy device 1, a control signal is sent to the stepper motor 5, by which rotation takes place such that the desired filter 2' travels to the position of the opening 8, i.e. to the position shown for filter 2 in front of the lamp 4. In this way, the filter is automatically selected by the controller without the operator himself having to replace it.

FIGS. 3(a) & 3(d) show another arrangement of the light irradiation unit 10'. A filter 22 is mounted in a slot 29. In this embodiment, there are three slots. A total of three filters can be arranged at the same time. The slot 29 is attached in a slot frame 28 which is attached by a magnet 21 in the phototherapy device and is provided with a handle 25. Furthermore, there is a pivot mechanism 27. As is shown at bottom left, the user can access the filter 22 by pulling the handle 25. As is shown in FIG. 3(c), in the region encircled by the broken line 23 which is shown in FIG. 3(d), downstream from the filter, there are concave portions G on a base 10'A. There is the following arrangement: When the filter 22 is replaced, another convex part H corresponding to the filter 22 projects from the slot 29 and fits into the corresponding one of the concave parts G of the base 10'A. Thus, the type of filter is determined. In this connection, the shape of the projection is shown only by way of example. The projection direction is not limited only to a direction parallel to the filter surface, but is essentially identical even if it is perpendicular to the filter surface.

Electrical switches are mounted in these concave portions G. Depending on which switch has reacted, an electrical signal is sent which shows which handle part has triggered the switch, i.e. which filter was mounted. This circumstance is not shown in the drawings. In view of this principle, not only the fit of the projecting and offset parts, but also a process is possible in which, for example, in one part of the contact region of the filter a metallic line is laid, this part acquiring a switching function and the electrical circuit located in the contact region being short circuited.

Figure 6:
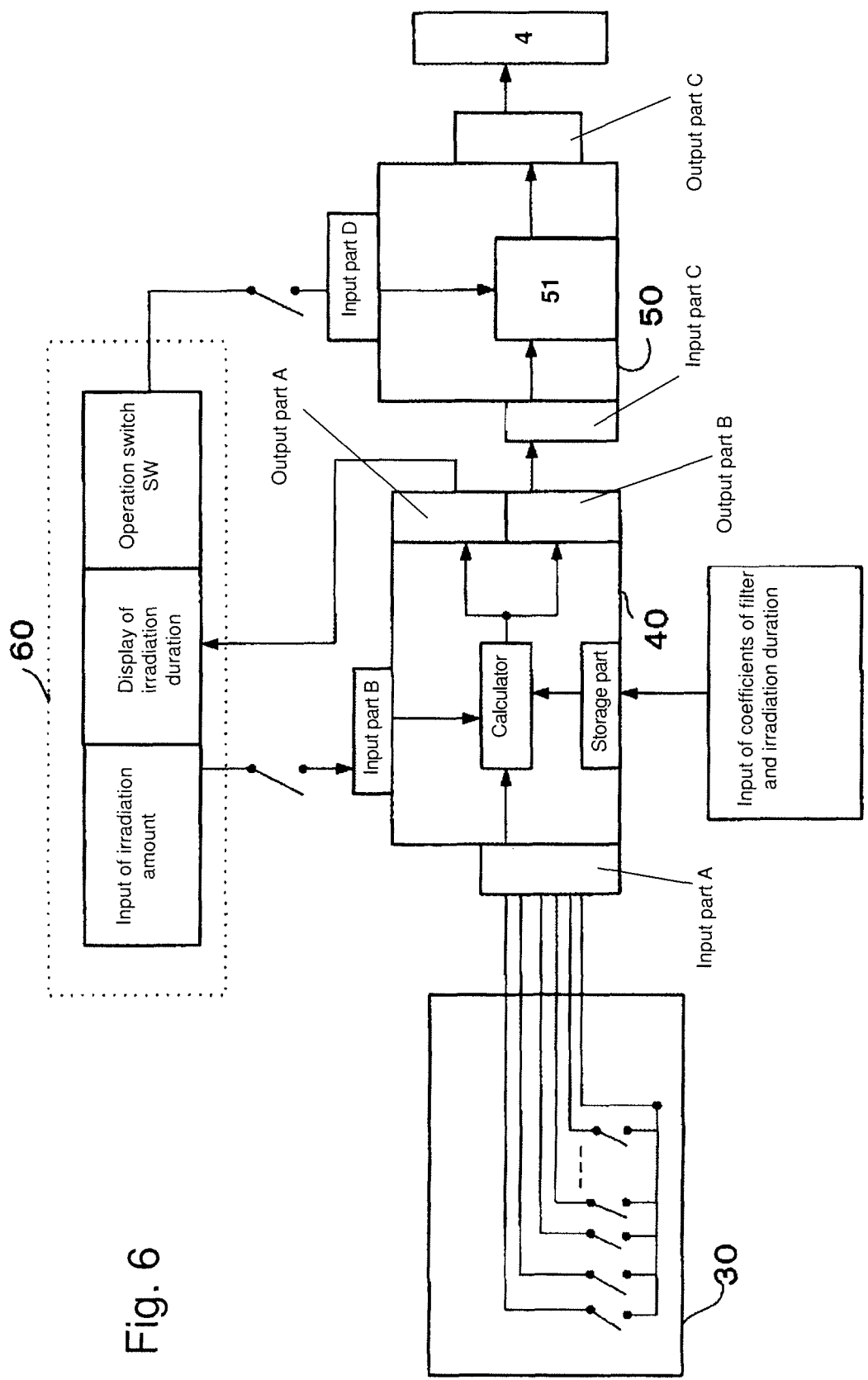
FIG. 6 is a block diagram of a device which controls the amount of irradiation of the phototherapy device in accordance with the invention using excimer radiation.

FIG. 6 is a block diagram illustrating the device for controlling the amount of irradiation of the phototherapy device in accordance with the invention using excimer radiation. A filter selecting circuit 30 is connected to the input part A of a microcomputer part 40 of the phototherapy device. When the filter is correctly arranged in the irradiation unit, the microcomputer part 40 electrically determines at the input part A which filter was attached.

In the microcomputer part 40, there is a memory in which coefficients are stored beforehand which increase/reduce irradiation duration depending on the filter type. In this connection, coefficients are calculated which consider both the relative change and the absolute change of the emission spectrum shape depending on the type of filter. When the operator (for example, nurse, caregiver or the like) inputs the amount of irradiation (unit J and the like) via a user interface 60, this signal together with an ON input of a confirmation switch by the operator is provided to an input part B of the microcomputer part 40.

The arithmetic-logic unit of the microcomputer part 40 computes a suitable irradiation duration depending on the filter type and the amount of irradiation, based on a coefficient by the filter type. The computed irradiation duration is sent to the output parts A and B of the microcomputer part 40. The irradiation duration sent to the output part A is sent to an irradiation duration display part of the user interface 60 and displayed such that the operator can confirm it. The irradiation duration sent to the output part B is sent to the input part C of a power source part 50. The irradiation duration sent to the input part C is sent to a timer circuit 51.

When the operator turns on an operating switch SW in the user interface 60, this ON signal triggers the timer circuit 51 via the input part D of the power source part. From triggering, an output is supplied during the irradiation duration according to the received signal via the input part C. The output is sent from the output part C of the power source part to the lamp 4. As was described above, a phototherapy device using excimer radiation is obtained for which, in spite of changing the types of filters, a suitable irradiation duration is automatically determined.

For effective use of the therapy effect, it is desirable to actively use radiation with short wavelengths of roughly 290 nm. However, the wavelengths in this range have powerful side effects and are also dangerous. The dependency on these wavelengths was studied by several researchers in the past. No decisive data, however, have been obtained. It can be considered that the reason is that the effects differ depending on individual differences, such as skin color, skin condition type and the like, and they also differ in a single patient depending on the skin sites. In an actual clinical environment, therefore, test irradiations of the patients are performed and treatment is carried out such that side effects are confirmed.

Figure 7:
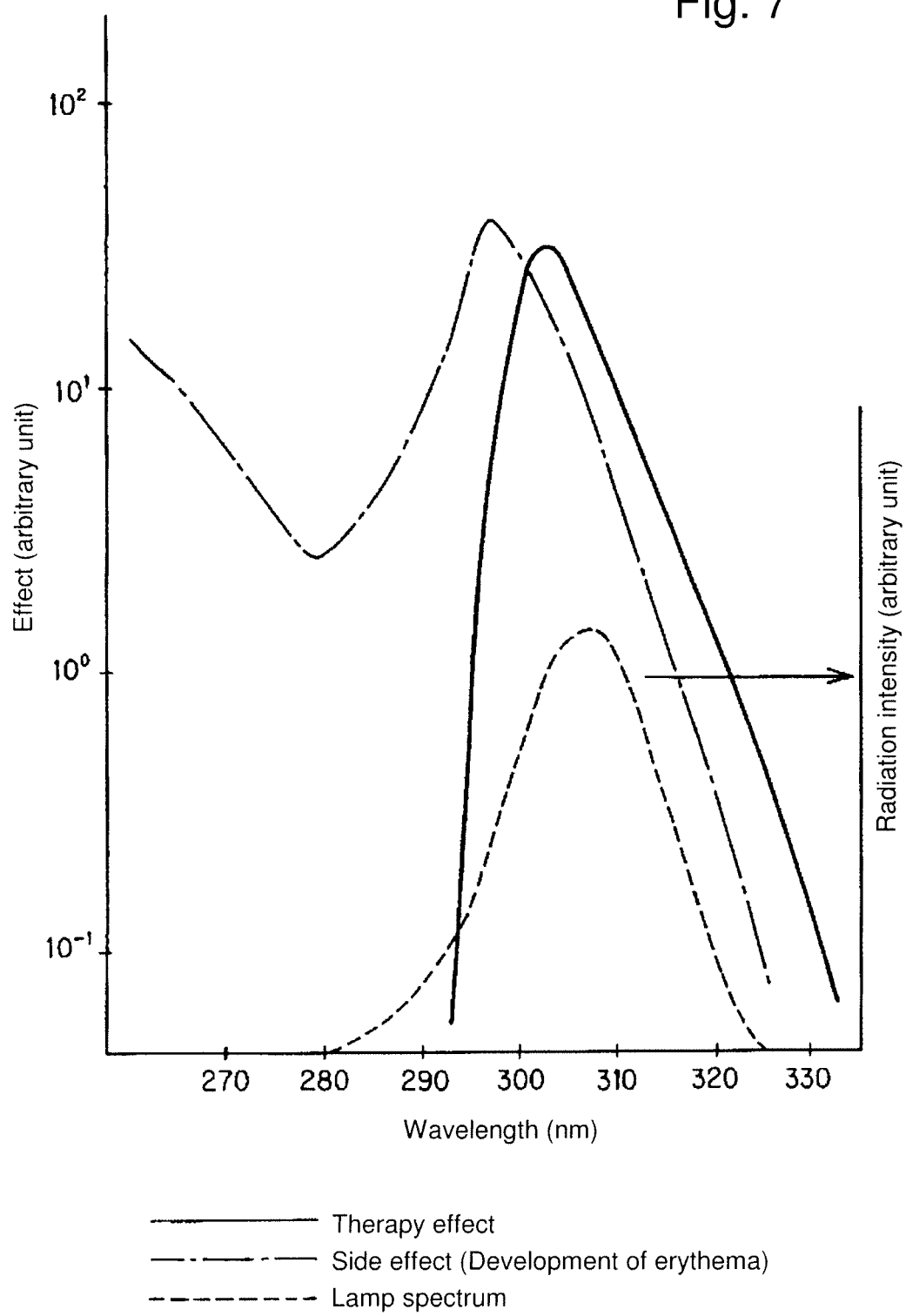
FIG. 7 is a graph of the wavelength dependency exhibited by the therapy effect for psoriasis and the wavelength dependency of the outbreak of erythema side effect and lamp spectrum.

The curves of effects shown in FIG. 7 change depending on sites and individuals to a large extent. It can be considered, in this connection, what influence this change has. When the sensitivity of the therapy effect is high, the curve of the therapy effect shifts upward overall, in this connection, with shorter wavelengths, it is possible to increase the therapy effect, not increasing the side effects. On the other hand, for low sensitivity of the therapy effect, side effects become stronger when radiation with longer wavelengths is not used; this inevitably burdens the patients.

For curves of the action of side effects it can likewise be easily assumed that depending on the sensitivity the optimum therapeutic wavelength range changes.

Figure 5A:
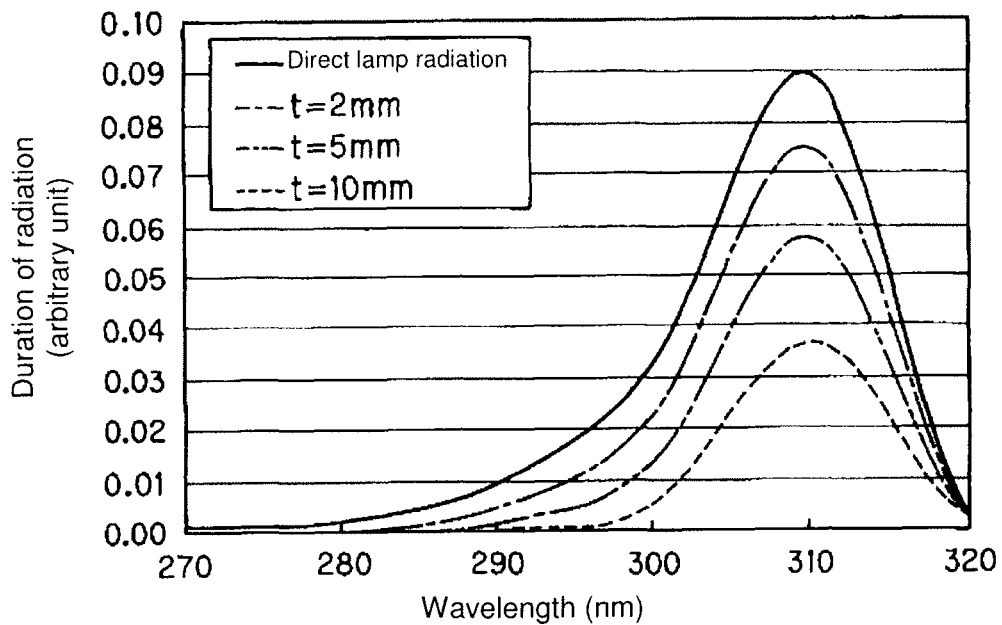
FIGS. 5(a) & 5(b) each show a graph of the change in the wavelength radiant light from the phototherapy device in accordance with the invention using excimer radiation and a filter of borosilicate glass of three filter thicknesses and uncontrolled irradiation without a filter.
Figure 5B:
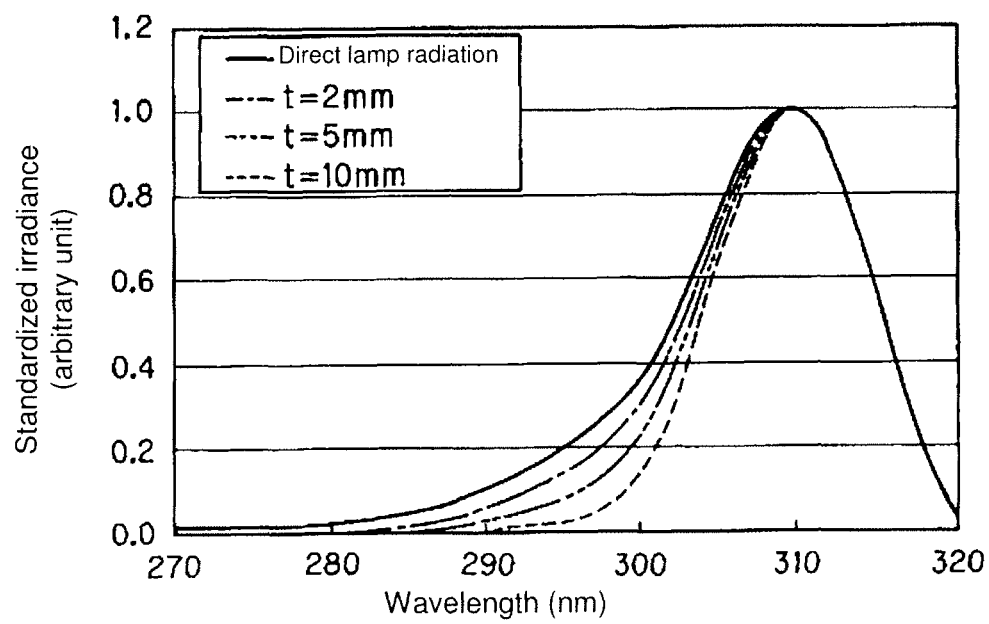

Therefore, when the patients are irradiated with only uncontrolled emission spectrum radiated from the lamp, it is not possible to adjust to different diseased sites on the patient and individual differences between the patients, and therefore, not possible to consistently administer optimum therapy. A phototherapy device using excimer radiation, in which especially the radiation intensity with short wavelengths of roughly 290 nm can be controlled, is therefore highly desirable. FIG. 5(*a*) shows how, using a borosilicate glass filter with a thickness which has been changed from 2 mm to 10 mm, the radiation of a XeCl excimer lamp changes. FIG. 5(*b*) shows the result for which FIG. 5(*a*) was normalized. This phototherapy device using excimer radiation in which filters with different properties can be chosen is an embodiment which is clinically a very advantageous embodiment. It is advantageous to replace the filter and to administer therapy such that the portion of the radiation with short wavelengths increases. The phototherapy device in accordance with the invention using excimer radiation enables irradiation with optimum wavelengths at which side effects can be suppressed by gradually increasing the portion of the radiation with short wavelengths. The greater the filter thickness, the weaker the radiation intensity becomes. The amount of irradiation in the required wavelength range is therefore controlled based on time.

One specific example of a filter is the case using the absorption property in which the glass contains borosilicate. The absorption property can be changed by fine alteration of its composition ratio. The absorption property can be changed in relative terms more easily, as was described above, by changing its thickness.

Figure 8:
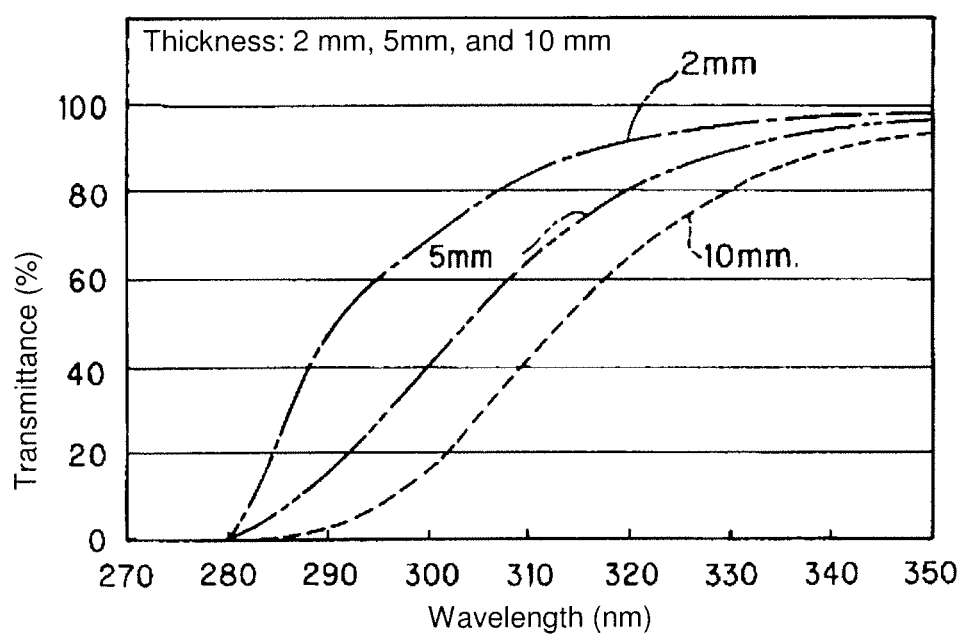
FIG. 8 is a graph of the light transmission of the UV-B range of a borosilicate filter, for example, which is used for the phototherapy device in accordance with the invention using excimer radiation.

FIG. 8 shows the property of transmittance of glass with a thickness which has been changed. The filter is mounted between the lamp and the diseased site on the patient and is used to change the lamp emission spectrum. The filter can be mounted in the form in which it serves as the front glass at the surface of the light irradiation unit, or it can be located between the lamp within the light irradiation unit 10 and the front glass of the light irradiation unit. Provided the emission spectrum of the lamp can be changed, there is no disadvantage.

The filter which is used for the phototherapy device in accordance with the invention using excimer radiation can also be, for example, water/oxygen-free aluminum fluoride glass, besides borosilicate glass. The specific compositions are described below.

For the glass, the component content in percent by mole of $BaF_2$, $CaF_2$, $AlF_3$ is in the range from 14.00 to 24.00, in the range from 28.25 to 38.25 and in the range from 37.25 to 47.25, respectively. The glass contains one of $YF_3$, $SrF_2$, $LaF_3$. The content of $YF_3$ is 2.5% by mole to 20% by mole, the content of $SrF_2$ is 2.5% by mole to 7.5% by mole and the content of $LaF_3$ is 2.5% by mole to 7.5% by mole. Furthermore Ce is contained. The glass is water/oxygen free. The Ce content is preferably 1% by at. to 10% by at.

What we claim is:

1. Phototherapy device using excimer radiation, comprising:
   a dielectric barrier discharge XeCl excimer lamp which radiates in the wavelength range of 270 nm to 320 nm for irradiation of diseased sites afflicted by a skin disorder with UV-B radiation, and
   an optical filter unit comprising at least one optical filter having a transmittance of 0% below a wavelength of 280 nm for changing the wavelength range and shape of the spectrum of the UV-B radiation with which the diseased sites are irradiated.

2. Phototherapy device using excimer radiation in accordance with claim 1, wherein the optical filter unit has several optical filters which can be selectively arranged in a beam path to change the shape of the spectrum of the UV-B radiation.

3. Phototherapy device using excimer radiation in accordance with claim 2, wherein the several optical filters are made of the same material but differ in their thickness.

4. Phototherapy device using excimer radiation in accordance with claim 3, wherein the optical filters are made of borosilicate glass.

5. Phototherapy device using excimer radiation in accordance with claim 2, wherein each of the several filters transmits a different wavelength.

6. Phototherapy device using excimer radiation in accordance with claim 1, wherein the at least one optical filter is selected from an assortment of several optical filters provided externally of the phototherapy device and is used for changing the shape of the spectrum of the UV-B radiation.

7. Phototherapy device using excimer radiation in accordance with claim 1, wherein the optical filter unit has a receiving area for holding the at least one optical filter from an assortment of several optical filters.

8. Phototherapy device using excimer radiation in accordance with claim 1, wherein the optical filter unit has a receiving area for holding the at least one optical filter from an assortment of several optical filters and wherein the several optical filters are made of the same material but differ in their thickness.

9. Phototherapy device using excimer radiation in accordance with claim 8, wherein the optical filters are made of borosilicate glass.

10. Phototherapy device using excimer radiation in accordance with claim 1, further comprising a device for controlling the amount of irradiation by changing an irradiation time according to the type of optical filter.

* * * * *